United States Patent [19]
Ben-Hur et al.

[11] Patent Number: 6,010,890
[45] Date of Patent: Jan. 4, 2000

[54] METHOD FOR VIRAL INACTIVATION AND COMPOSITIONS FOR USE IN SAME

[75] Inventors: Ehud Ben-Hur; Maria M. Zuk, both of New York, N.Y.

[73] Assignee: New York Blood Center, Inc., New York, N.Y.

[21] Appl. No.: 08/841,115

[22] Filed: Apr. 29, 1997

[51] Int. Cl.[7] ............................. C12N 13/00; A01N 1/02
[52] U.S. Cl. ................................. 435/173.3; 435/173.1; 435/2
[58] Field of Search ...................... 435/2, 173.1, 173.3

[56] References Cited

U.S. PATENT DOCUMENTS

| | | | |
|---|---|---|---|
| 4,873,088 | 10/1989 | Mayhew et al. | 424/450 |
| 5,010,073 | 4/1991 | Kappas et al. | 514/485 |
| 5,023,087 | 6/1991 | Yau-Young et al. | 424/450 |
| 5,089,181 | 2/1992 | Hauser | 424/1.21 |
| 5,109,016 | 4/1992 | Dixon et al. | 514/410 |
| 5,232,844 | 8/1993 | Horowitz et al. | 435/173.1 |
| 5,238,940 | 8/1993 | Liu et al. | 514/410 |
| 5,277,913 | 1/1994 | Thompson et al. | 424/450 |
| 5,281,616 | 1/1994 | Dixon et al. | 514/410 |
| 5,389,378 | 2/1995 | Madden | 424/450 |
| 5,407,808 | 4/1995 | Halling et al. | 435/34 |
| 5,484,778 | 1/1996 | Kenney et al. | 514/63 |
| 5,484,803 | 1/1996 | Richter et al. | 514/410 |
| 5,516,629 | 5/1996 | Park et al. | 435/2 |
| 5,556,612 | 9/1996 | Anderson et al. | 424/59 |
| 5,599,831 | 2/1997 | Poretz et al. | 514/410 |
| 5,705,518 | 1/1998 | Richter et al. | 514/410 |

OTHER PUBLICATIONS

Terrian (1996) Diss. Abs. Intl., 58(3b), "The Photochemistry and Photobiology of Phodium(III) polypyridl Complexes and Psoralen Pro–Drugs", p. 1276, in DISSABS, AN 97:54736.

Henderson (May 19, 1997) Blood Weekly, "Conference Coverage (Blood Safety) Pc4 Selectively Inactivates Viruses", in PROMT, AN 97:290581.

Morgan et al. (1992) Brit. J. Cancer, 65(1), "Use of Photosensitive, Antibody Directed Liposomes to Destroy Target Populations of Cells in Bone Marrow: A Potential Purging Method for Autologous Bone Marrow Transplantation", pp. 58–64.

*Primary Examiner*—Jon P. Weber
*Attorney, Agent, or Firm*—Amster, Rothstein & Ebenstein

[57] ABSTRACT

The present invention provides methods for reducing the level of infectious virus contained in red blood cell compositions. The methods comprise the steps of contacting the composition with a photosensitizer formulated in a liposome carrier, and exposing the composition to light at a sufficient wavelength, dose and duration to reduce the level of infectious virus contained in the composition. In the methods of the present invention, a quencher, either alone or formulated in a liposome carrier, also may be added to the red blood cell composition before application of light. The present invention also provides compositions containing photosensitizers formulated in specific liposome carriers, as well as quenchers formulated in liposome carriers, for use in the methods of the present invention.

28 Claims, 8 Drawing Sheets

METHOD FOR VIRAL INACTIVATION AND COMPOSITIONS FOR USE IN SAME

STATEMENT OF GOVERNMENT INTEREST

This invention was made with government support under NIH Grant No. 2RO1-HL41221. As such, the government has certain rights in this invention.

BACKGROUND OF THE INVENTION

Improvements in current practices of viral marker screening and donor self-exclusion are continuously increasing the safety of the blood supply. However, despite these practices, a risk of transmission of pathogens with the transfusion of cellular components of blood remains since current screening tests do not screen for rarely occurring or as yet unknown transfusion transmissible pathogens (Dodd, R. Y. *New Engl. J. Med.* 327:419–421 (1992); Soland, E. M., et al. *J. Am. Med. Assoc.* 274:1368–1373 (1995); Schreiber, G. B., et al. *New Engl. J. Med.* 334:1685–1690 (1996)).

To combat the deficiencies associated with screening practices, the use of sterilization procedures of blood, red blood cell concentrates (RBCC), and other blood-derived components hold promise for eliminating pathogen transmission. In this connection, various approaches have been used to sterilize blood cells, the most efficacious so far use photochemical methods (Ben-Hur, E. and B. Horowitz *Photochem. Photobiol.* 62:383–388 (1995); Ben-Hur, E. and B. Horowitz *AIDS* 10:1183–1190 (1996)). The most promising photochemical methods employ the use of phthalocyanines (which are activated by light in the far red (660–700 nm)) for sterilization of RBCC (Horowitz, B., et al. *Transfusion* 31:102–108 (1991); Ben-Hur, E., et al. *J. Photochem. Photobiol. B:Biol.* 13:145–152 (1992)).

Of the phthalocyanines, silicon phthalocyanine Pc4 has been proven to be most effective for inactivation of HIV in its multiple forms (Margolis-Nunno, H., et al. *Transfusion* 36:743–750 (1996)). However, because Pc4 and other phthalocyanines target the lipid envelope of viruses and can, therefore, cause red cell damage, quenchers of reactive oxygen species have been used to prevent some of this damage (Rywkin, S., et al. *Photochem. Photobiol.* 56:463–469 (1992); Ben-Hur, E., et al. *Transfusion* 35:401–406 (1995)). The use of high irradiance (Ben-Hur, et al. *Photochem. Photobiol.* 61:190–195 (1995)) and Chremophor as the vehicle (Ben-Hur, et al. *Photochem. Photobiol.* 62:575–579 (1995)) also improved the specificity of viral sterilization by Pc4.

SUMMARY OF THE INVENTION

The present invention is directed to an improvement for reducing the level of infectious virus that may be contained in a red blood cell composition, while simultaneously reducing the damage to red blood cells. Specifically, the inventors of the present invention have found that by incorporating the photosensitizer in a liposome carrier, the photosensitizer is more specific to the infectious virus, and at the same time, reduces the damage to red blood cells.

Accordingly, the present invention provides a method for reducing the level of infectious virus contained in a red blood cell composition comprising the steps of contacting the composition with a photosensitizer formulated in a liposome carrier, and exposing the composition to light at a sufficient wavelength, dose and duration to reduce the level of infectious virus contained in the composition.

The present invention also provides a method for reducing the level of infectious virus contained in a red blood cell composition comprising the steps of contacting the composition with (i) a photosensitizer formulated in a liposome carrier, and (ii) a quencher, and exposing the composition to light at a sufficient wavelength, dose and duration to reduce the level of infectious virus contained in the composition.

In addition, the inventors of the present invention have found that by incorporating the quencher in a liposome carrier, and using the same along with the photosensitizer formulated in a liposome carrier, a substantial reduction in the level of infectious virus can be obtained without substantial harm to the red blood cells.

Accordingly, the present invention also provides a method for reducing the level of infectious virus contained in a red blood cell composition comprising the steps of contacting the composition with (i) a photosensitizer formulated in a liposome carrier, and (ii) a quencher formulated in a liposome carrier, and exposing the composition to light at a sufficient wavelength, dose and duration to reduce the level of infectious virus contained in the composition.

The present invention further provides compositions containing photosensitizers formulated in specific liposome carriers, as well as quenchers formulated in liposome carriers, for use in the methods of the present invention.

Additional objects of the present invention will be apparent from the description which follows.

DETAILED DESCRIPTION OF THE INVENTION

The present invention provides a method for reducing the level of infectious virus that may be contained in a red blood cell composition. The method comprises the steps of contacting the composition with a photosensitizer formulated in a liposome carrier, and exposing the composition to light at a sufficient wavelength, dose and duration to reduce the level of infectious virus contained in the composition.

As used herein, "red blood cell composition" includes whole blood, RBCC and any other composition that contains red blood cells. "Virus" includes human immunodeficiency virus, Cytomegalovirus, Ebstein-Barr virus, Hepatitis B virus, Hepatitis C virus, Herpes Simplex type I and II viruses, and other viruses that circulate in freely in the composition, as well as cell-associated viruses. "Reducing the level of infectious virus'" means that the all or substantially all of the infectious virus is destroyed or inactivated.

Suitable photosensitizers include but are not limited to phthalocyanines, porphyrins, purpurins, psoralens, bergaptens, angelicins, chlorins and flavins. Particularly preferred photosensitizers are those compounds which absorb in the red region of the visible spectrum such as phthalocyanines. Suitable phthalocyanines include but are not limited to phthalocyanines containing a central atom of aluminum, germanium, gallium, tin or silicon such as silicon phthalocyanine (i.e. hydroxysiloxydimethylpropyl-N-dimethyl silicon phthalocyanine, "Pc4")), as well as sulfonated or nitrated forms of such pthalocyanines, such as sulfonated aluminum phthalocyanine (i.e. aluminum tetrasulfophthalocyanine ("AlPcS$_4$") or aluminum disulfophthalocyanine ("AlPcS$_{2a}$"). Such phthalocyanines and others are described in Spikes, J. *Photochemistry and Photobiology* 43:691–699 (1986); Ben-Hur, E. and Rosenthal, I. *Int. J. Radiat. Biol.* 47:145–147 (1985); Moser, F. H. and Thomas, A. C. *The Phthalocyanines*, Boca Raton, CRC Press, 1984; Kreimer-Birnbaum, M. *Sem. Hematol.* 26:157–193 (1989); and U.S. Pat. Nos. 5,120,649, 5,232,844 and 5,484,778, which are hereby incorporated by reference in their entirety. In the most preferred embodiment, the photosensitizer is Pc4.

The photosensitizer may be formulated in the liposome carrier by mixing the desired amount of the photosensitizer with the liposome carrier using procedures well known in the prior art. The liposome carrier may comprise at least one natural phospholipid (e.g. soy phosphatidyl choline), at least one synthetic phospholipid, or combinations thereof. Suitable synthetic liposome carriers include but are not limited to one or more of the following: 1-palmitoyl-2-oleoyl-sn-glycero-phosphocholine (POPC), 1,2-dioleoyl-sn-glycero-3-[phospho-L-serine] (DOPS), 1,2-dioleolyl-sn-glycero-3-phosphate (PA), 1, 2-dipalmitoyl-sn-glycero-3-phosphocholine (DPPC), 1,2-distearyl-sn-glycero-3-[phospho-rac-(1-glycerol)] sodium salt (DSPG), and 1, 2-distearyl-sn-glycero-3-phosphocholine (DSPC). Preferably, the liposome carrier comprises POPC and DOPS at a ratio of 10:1–0.5:1. Most preferably, POPC and DOPS are used at a ratio of about 4:1, since this results in the least amount of damage to red blood cells.

The photosensitizer is added to the red blood cell composition in an amount effective to undergo a reaction and damage or destroy infectious virus upon application of light at a sufficient wavelength, dose and duration. The specific concentration will depend upon the photosensitizer chosen. However, the inventors have found that when Pc4 is the photosensitizer, the ratio of Pc4:liposome should be about 1:100–1:10. The final concentration of PC4 in the red blood cell composition is preferably about 0.5–10 μM, and most preferably is about 1–5 μM.

After the photosensitizer/liposome formulation is added to the red blood cell composition, it is desirable not to wait too long before applying light. The inventors have found that the longer the photosensitizer/liposome formulation is in contact with the red blood cell composition, the more likely it will dissolve releasing the photosensitizer into the composition, and causing hemolysis of the red blood cells. Accordingly, the inventors have found that light should be applied within 30 minutes, more preferably within about 10 minutes, and most preferably within about 5 minutes, after adding the photosensitizer/liposome formulation to the red blood cell composition.

The light is applied at a sufficient wavelength, dose and duration to reduce the level of infectious virus contained in the composition. It is preferred that this wavelength, dose and duration is chosen to maximize the inactivation of infectious virus, and at the same time, to minimize the damage to the red blood cells. The wavelength of light applied preferably corresponds to the maximum absorption of the photosensitizer. For example, when the photosensitizer is Pc4, it is preferred that the light be applied at a specific wavelength somewhere in the range of 665–705 nm, and most preferably at a specific wavelength in the range of 670–680 nm. The dose of light applied depends upon the volume of the red blood cell composition to be treated, and can range anywhere from 5 J/cm² to 200 J/cm². At such doses of light, the composition can be treated for 5 minutes to 3 hours, and preferably for 10 minutes to 1 hour. For volumes of 50 ml, and using Pc4 as the photosensitizer, the inventors have found that the application of light at a wavelength of about 675 nm, at dose of 55 J/cm2, for a duration of 10 minutes, results in the best viral reduction of HIV with the least amount of RBC hemolysis. Suitable sources of light include commercially available lasers, lamps, light emitting diodes and the like. Preferably, a LED arrays (Efos Canada, Inc., Mississauga, Ontario, Canada) is employed. To achieve the desired wavelength of light, the lamp may be equipped with commercially available filters.

It also is within the confines of the present invention that one or more quenchers can be added to the red blood cell composition before, during or after the addition of the photosensitizer/liposome formulation. Suitable quenchers include but are not limited to glutathione, trolox, flavonoids, vitamin C, vitamin E, cysteine and ergothioneine and other non-toxic quenchers. The concentration of the quencher contained in the red blood cell composition will depend upon the specific quencher(s) chosen and can be determined by one skilled in the art. However, when the quencher is vitamin E, the preferred concentration ranges from 0.1 mM to 2 mM, and is most preferably 1 mM.

In addition, it is within the confines of the present invention that one or more quenchers can be formulated in a liposome carrier to enhance the association of the quencher to the red blood cells, thus affording a more selective protection to the red blood cells. Suitable liposome carriers include those carriers that enhance delivery of the quencher to the red blood cells, such as liposomes containing cholesterol, liposomes made from natural phospholipids (e.g. soy phosphatidyl choline (PC)), and POPC. Preferably, the quencher is vitamin E, and the liposome carrier is POPC. When using vitamin E and POPC, the preferred vitamin E:POPC ratio is 1:5–1:3, and most preferably is about 1:3.7.

The present invention is described in the following Examples which are set forth to aid in an understanding of the invention, and should not be construed to limit in any way the invention as defined in the claims which follow thereafter.

EXAMPLE 1

Materials and Methods
Preparation of Pc4 in Liposomes.

The following procedure describes the preparation of $HOSiPcOSi(CH_3)_2(CH_2)_3N(CH_3)_2$ (Pc4) in liposomes composed of phosphatidyl choline and phosphatidyl serine. Pc4 (1 mg) was dissolved in 0.5 ml of N-methylpyrolidone (NMP) prewarmed to 50° C. and sonicated 1–2 minutes. 1-palmitoyl-2-oleoyl-sn-glycero-phosphocholine (POPC) (90 mg) was dissolved in tert-butyl alcohol (0.5 ml), and prewarmed to 50° C. Similarly, 1,2-dioleoyl-sn-glycero-3-phospho-L-serine (DOPS) (10 mg) was dissolved in tert-butyl alcohol (0.5 ml), and prewarmed to 50° C. The solutions were then sonicated at 50° C. until complete dissolution occurred. The phospholipid solutions were combined and kept at 50° C. The Pc4 solution was combined with the phospholipid solution at 50° C. to achieve a ratio of Pc4:phospholipid=1:100 (w/w). This was mixed with excess (16×) of aqueous solution containing 9.45% D-lactose and 0.027% NaCl. Prior to mixing, the organic solution should be at 50° C. and the aqueous solution at 4° C. The former was added dropwise into the latter with vigorous stirring. Stirring was continued for 15 minutes at 4° C. The resulting liposomal suspension was concentrated (10×) with 100 kDa Amicon concentrator and centrifuged at 3000 rpm at room temperature. The remaining organic solvents were removed by dialysis against lactose/NaCl solution at 4° C. using a dialysis membrane with a MW cutoff of 6000–8000. The dialysis solution was changed 3×every few hours. The final liposomal solution of Pc4 was lyophilized and stored at 4° C. Prior to use, the liposomes were dissolved in phosphate buffered saline (PBS) using a vortex for mixing followed by 1–2 minutes of sonication.

The same procedure was used to prepare Pc4 in liposomes of various other compositions by substituting POPC and DOPS with the following: 1,2-dioleolyl-sn-glycero-3-phosphate (PA); 1,2-dipalmitoyl-sn-glycero-3-phosphocholine (DPPC); 1,2-distearyl-sn-glycero-3-[phospho-rac-(1-glycerol)] sodium salt (DSPG); 1,2-distearyl-sn-glycero-3-phosphocholine (DSPC); cholesterol (chol) and 1-palmitoyl-2-oleoyl-sn-glycero-3-phosphoethanolamine-N-[poly(ethyleneglycol) 5000] (PEG).

Photodynamic Treatment.

RBCC samples (3 ml in polystyrene tubes) at hematocrit of 58–60% in ADSOL (obtained from Blood Services, New York Blood Center) were irradiated with red light either as a broad band (600–800 nm) or as a narrow band at 668 nm or 700 nm. Broad band light was from a 300 W xenon lamp (Oriel Corp., Stratford, Conn.) equipped with a cutoff filter ($\lambda$>600 nm) with an irradiance of 25 mW/cm$^2$. Narrow band light (27 nm bandwidth at half-height) was from LED arrays (Efos Canada, Inc., Mississauga, Ontario, Canada) emitting at either 668 nm or 700 nm with an irradiance of 50 mW/cm$^2$. During irradiation the samples were rotated and rolled on a hematology mixer (Fisher Scientific, Inc., Pittsburgh, Pa.) to obtain even exposure. Temperature was kept at 25 or 4° C. by an air stream of appropriate temperature.

Virus Inactivation.

Inactivation of VSV in RBCC was studied using a standard infectivity assay (Margolis-Nunno, H., et al. *Transfusion* 36:743–750 (1996)). Prior to photodynamic treatment, RBCC samples were spiked with $10^7$ infectious units per ml together with Pc4 at 2 $\mu$M final concentration and the quenchers glutathione and trolex at 4 and 5 mM, respectively. After treatment, samples were diluted 10-fold with Dulbecco's modified Eagle's medium containing 5% fetal calf serum and centrifuged at 1900 rpm for 5 minutes to remove the red cells. The supernatants were sterile filtered using 0.22 $\mu$m filters (Millipore, Bedford, Mass.) and either stored at −80° C. or assayed immediately for virus infectivity.

Pc4 Analysis in RBCC.

The amount of Pc4 bound to RBC in the RBCC was measured using HPLC and extraction procedure described previously (Zuk, M. M., et al. *J. Chromat. B Biomed. Appl.* 673:220–224 (1995)). Amount of Pc4 was expressed as a percentage of the total recovered in RBCC. Recovery of Pc4 was about 90% (±10%).

RBC Hemolysis.

Samples of RBCC were stored after treatment at 4° C. The extent of hemolysis was determined by comparing the hemoglobin in the supernatant to the total hemoglobin. The total hemoglobin was determined by using the Drabkin reagent (Sigma Procedure #525, Sigma Chemical Co., St. Louis, Mo.). The absorption at 540 nm was used to calculate the amount of hemoglobin released in the supernatant.

Circulatory Survival of RBC.

Rabbit RBCC were treated as described for human red cells and their circulatory survival was determined as described previously (Rywkin, S., et al. *Photochem. Photobiol.* 56:463–469 (1992)). Briefly, treated red cells were labelled with 1 $\mu$Ci/ml Na$_2$ $^{51}$CrO$_4$ for 1 hour at room temperature and then thoroughly washed with PBS. The labelled cells were infused autologously. At intervals, 1 ml blood was withdrawn and the radioactivity associated with RBC was determined.

Results

Figure 1:
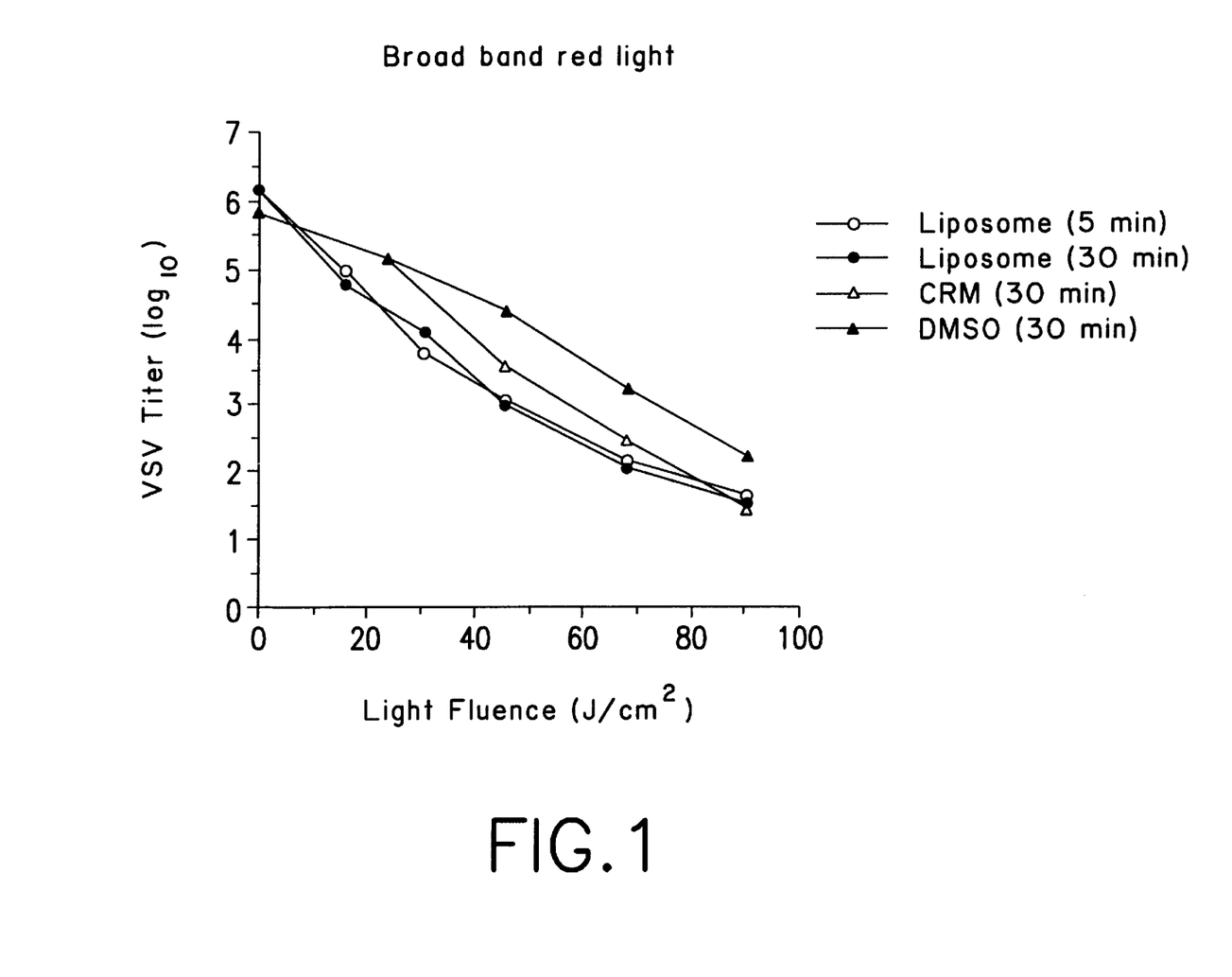
FIG. 1 represents inactivation of VSV in RBCC. Pc4 was added in the indicated delivery vehicle at a final concentration of 2 $\mu$M and exposed to a broad band of red light at room temperature as described in the Materials and Methods. Pre-irradiation incubation time at room temperature is indicated.
Figure 2:
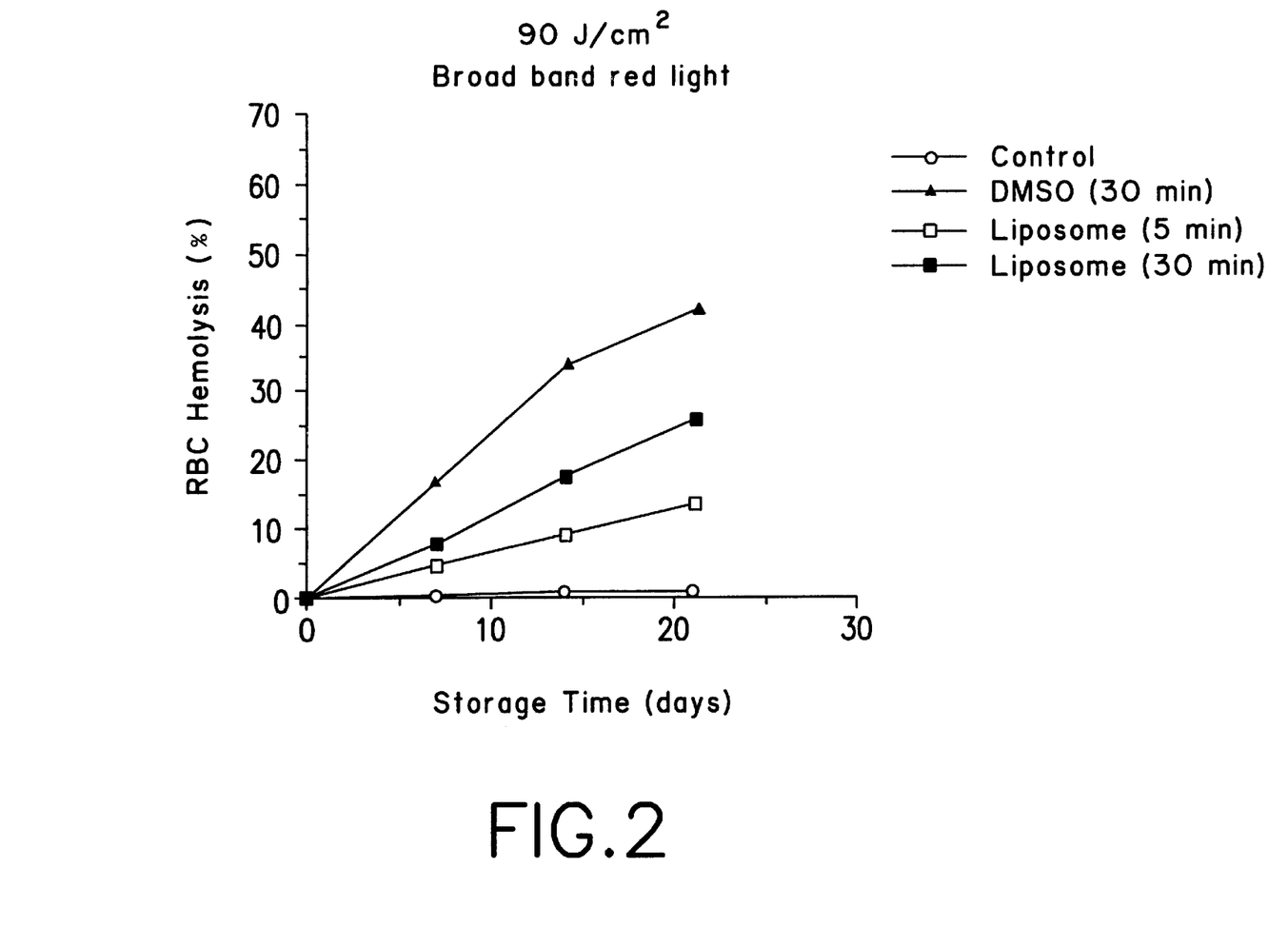
FIG. 2 represents RBC hemolysis during storage following virucidal treatment. Pc4 was added into RBCC in the indicated delivery vehicle at a final concentration of 2 $\mu$M and exposed to 90 J/cm2 broad band red light at room temperature after the indicated incubation time at room temperature. The treated RBCC were stored at 4° C. prior to assay.

The usefulness of liposomes as a delivery vehicle for Pc4 as a photosensitizer for inactivation of lipid-enveloped viruses in RBCC was assessed using VSV as a model virus. FIG. 1 shows that the rate of inactivation of VSV does not depend on time of incubation of liposomal Pc4 prior to light exposure and that it is similar to that obtained when Pc4 is delivered in an organic solvent (DMSO) or in a detergent-like agent (Cremophor). However, binding of Pc4 to red cells does depend on the delivery vehicle and, in the case of liposomes, on the pre-irradiation incubation time (Table 1). These results suggested that exposure to light after short incubation times with liposomal Pc4 should result in less damage to red cells. FIG. 2 shows this is indeed the case. Treated red cells were stored and their hemolysis followed, and as expected from the binding studies, formulation of Pc4 in liposomes resulted in less hemolysis, and incubation for 5 minutes was better than for 30 minutes.

Figure 3:
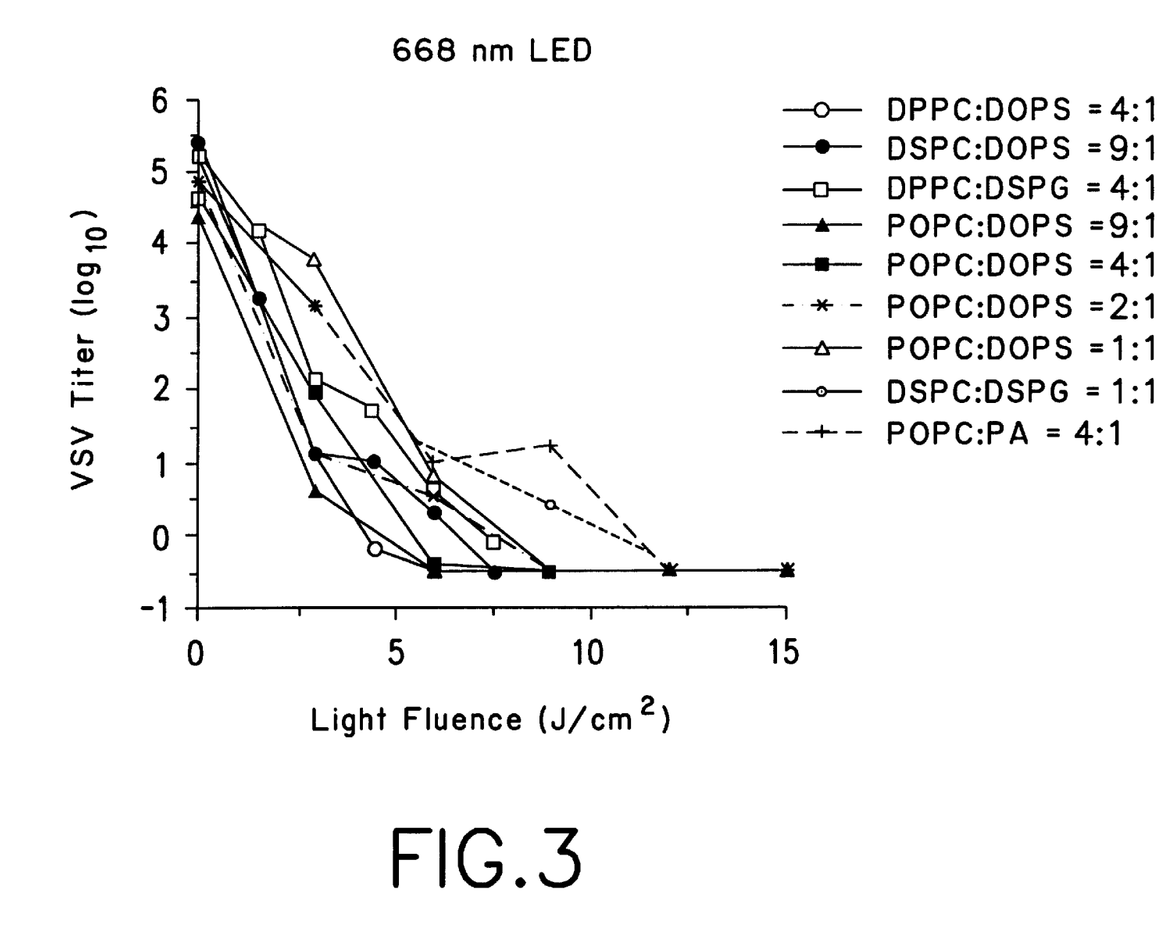
FIG. 3 represents VSV inactivation in RBCC by Pc4 and red light. Pc4 was added to RBCC in the indicated liposomal formulations at 2 $\mu$M and exposed to 668 nm light at room temperature after 5 minutes incubation.
Figure 4:
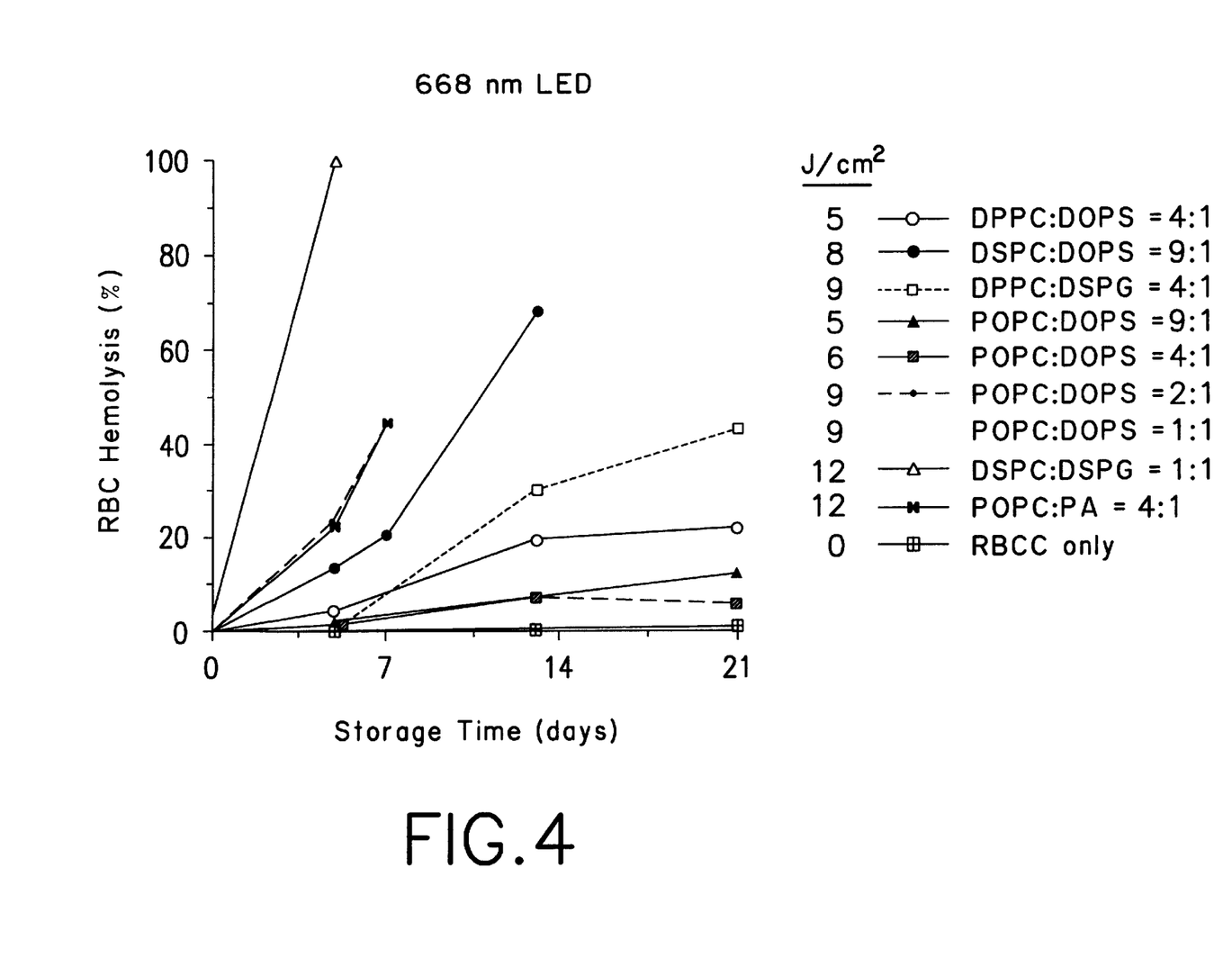
FIG. 4 represents RBC hemolysis during storage following virucidal treatment. PC4 was added to RBCC in the indicated liposomal formulations at 2 $\mu$M and exposed to 668 nm light at room temperature and the indicated dose after 5 minutes incubation. The treated RBCC were stored at 4° C. prior to assay.
Figure 5:
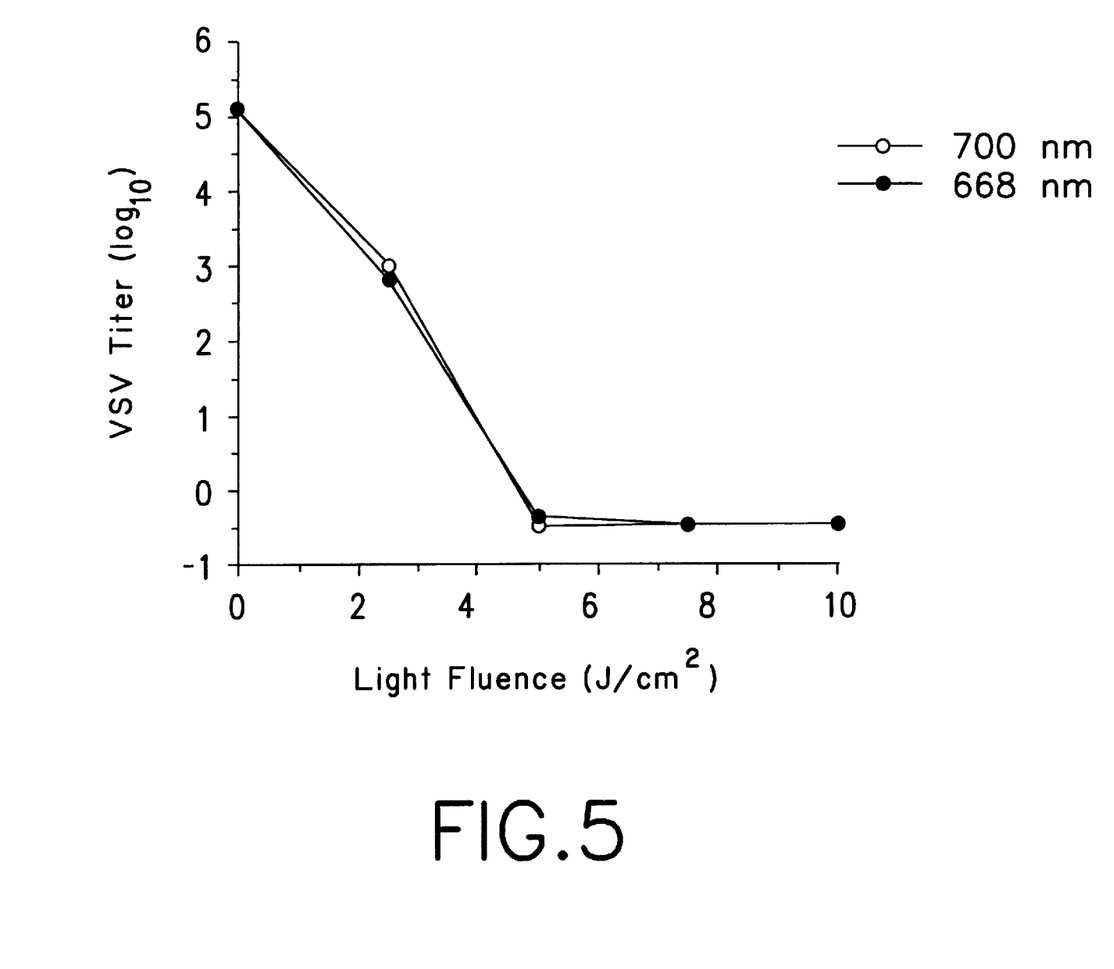
FIG. 5 represents inactivation of VSV in RBCC. Pc4 was added to RBCC in POPC:DOPS=4:1 liposomes at 2 $\mu$M and exposed to either 668 or 700 nm light at 4° C. after 5 minutes incubation at 4° C.
Figure 6:
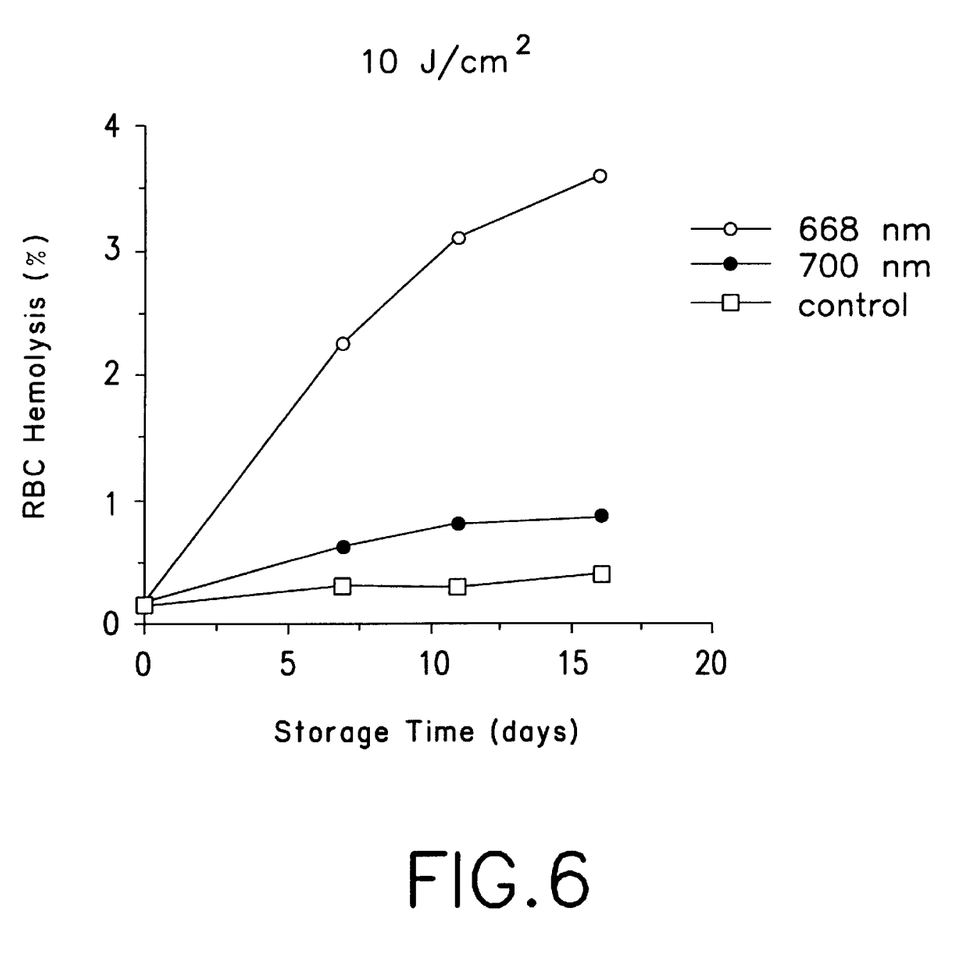
FIG. 6 represents RBC hemolysis during storage following virucidal treatment. Pc4 was added to RBCC in POPC:DOPS=4:1 liposomes at 2 $\mu$M and exposed to 10 J/cm$^2$ of either 668 or 700 nm light at 4° C. after 5 minutes incubation at 4° C. The treated RBCC were stored at 4° C. prior to assay.
Figure 7:
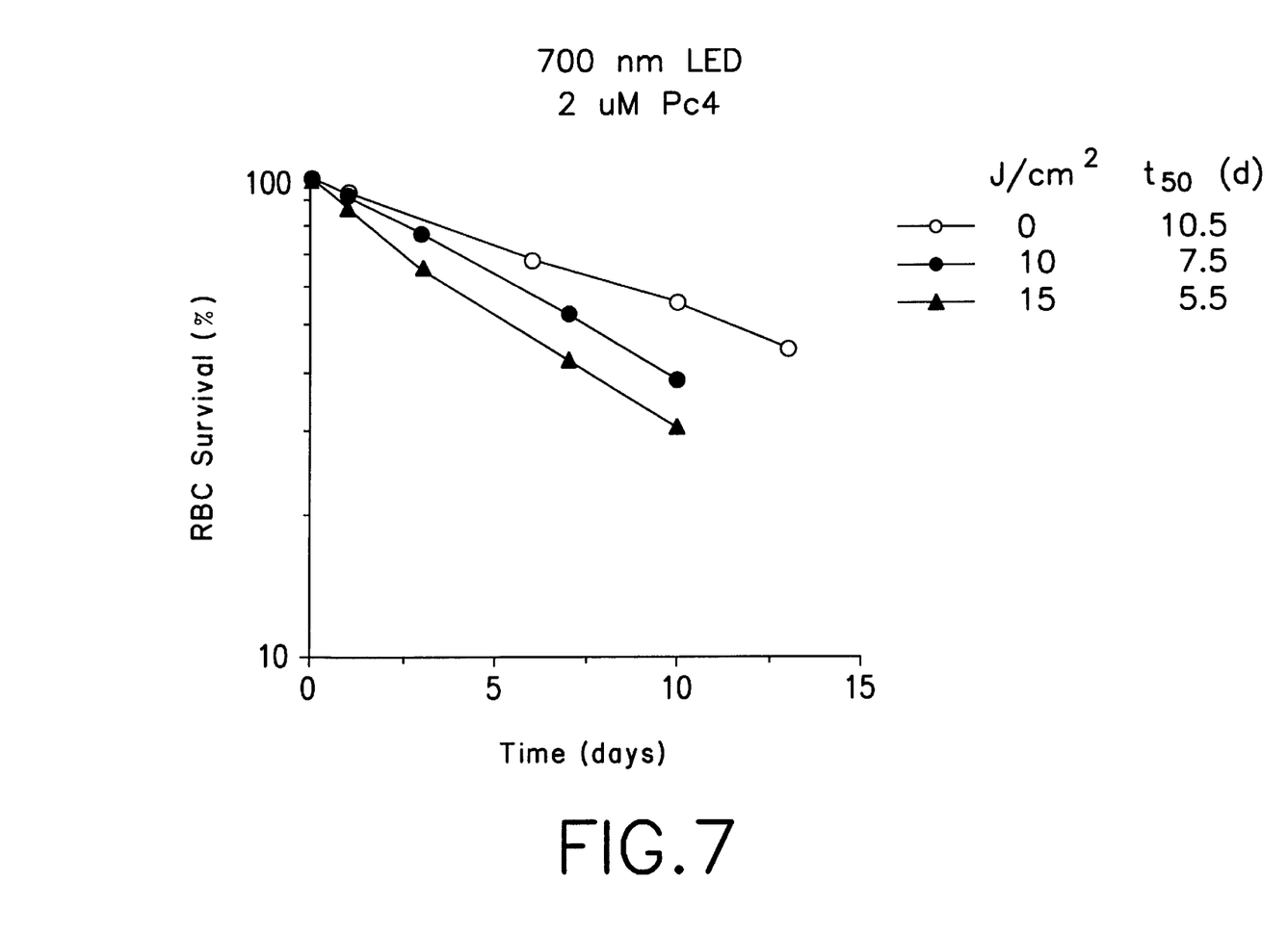
FIG. 7 represents circulatory survival of rabbit RBC after virucidal treatment. Pc4 was added to rabbit RBCC in POPC:DOPS=4:1 liposomes at 2 $\mu$M and exposed to 0, 10 and 15 J/cm$^2$, as indicated, of 700 nm light at room temperature after 5 minutes pre-irradiation incubation. The treated RBCC were labeled with $^{51}CrO^{2-}$ and their circulatory survival assayed as described in Materials and Methods.
Figure 8:
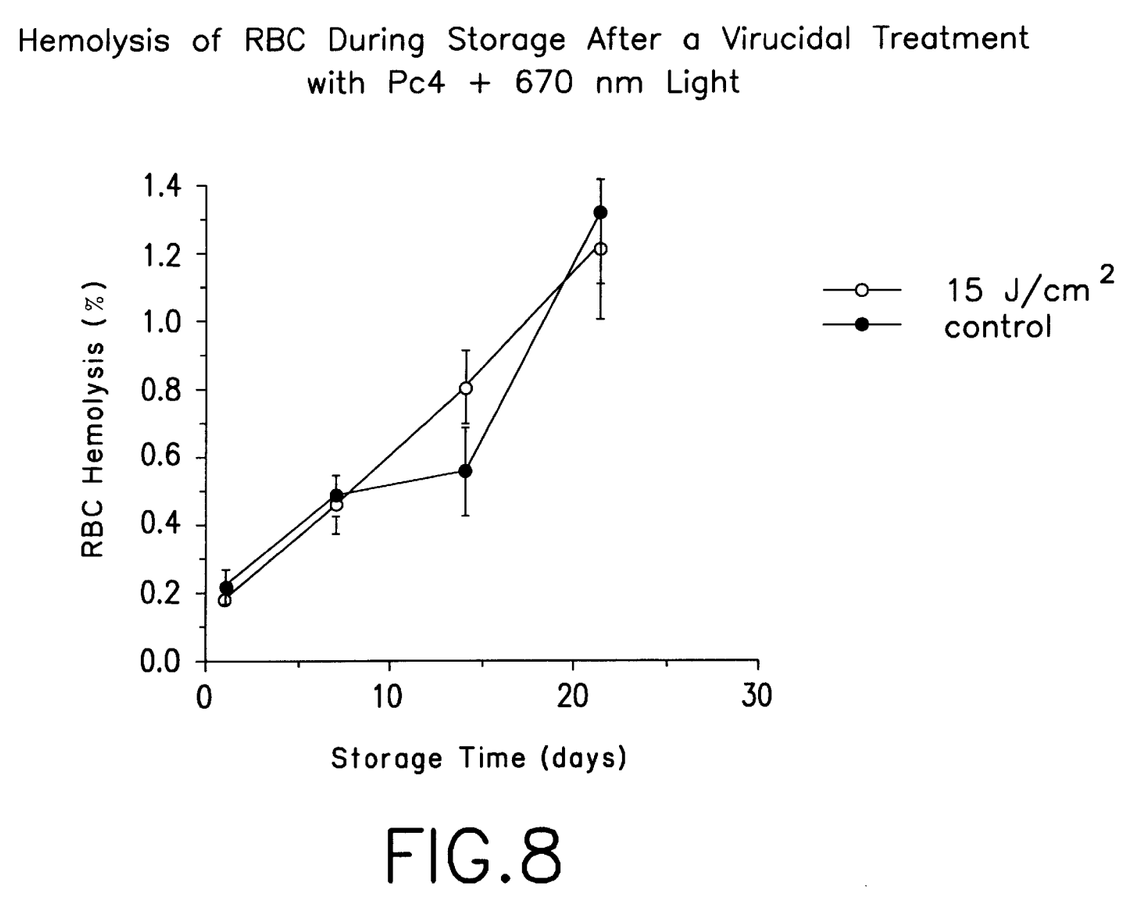
FIG. 8 represents RBC hemolysis during storage following virucidal treatment. Pc4 was added to RBCC in POPC:DOPS=4:1 liposomes at 2 μM, together with 4 mM cysteine, 1 mM tocopherol succinate and 0.5 mM carnitine. Light exposure was at 670 nm from LED array at a dose of 15 J/cm². The control was untreated RBCC.

The effect of the liposome composition on Pc4 binding to red cells is shown in Table 2. There were large differences in binding depending on composition. Compositions containing PEG or cholesterol displayed greatly enhanced binding. This was also reflected in greatly enhanced hemolysis of red cells (data not shown). Comparision of Tables 1 and 2 shows that Pc4 in POPC:DOPS=9:1 at room temperature is more binding to RBC than at 4° C. VSV kill was not affected by the incubation temperature. Liposomal compositions showing reduced Pc4 binding to red cells were compared with respect to VSV inactivation (FIG. 3). There was about 2-fold difference in the dose required for complete virus kill (≧5 $log_{10}$), 5–12 J/$cm^2$. For each liposomal preparation tested in FIG. 3, and equivirucidal light dose resulting in complete VSV kill was used to test RBC damage. The treated RBCC were stored after treatment and hemolysis followed over time. The results (FIG. 4) show great differences in the ability of equivirucidal doses to cause RBC damage, depending on the liposome composition. Since POPC:DOPS=4:1 resulted in least RBC damage, this composition was chosen for further studies.

In further studies, LED arrays emitting at either 668 or 700 nm were compared. FIG. 5 shows that both light sources were equally effective for inactivation of VSV. However, when RBCC were treated with 10 J/$cm^2$ from either light source and then stored at 4° C., hemolysis developed in samples treated with 668 nm LED much faster than in those treated with 700 nm LED (FIG. 6). In the latter, the rate of hemolysis was only slightly faster than in control, untreated RBCC.

The ability of treated RBC to circulate in vivo was tested in rabbits and in baboons. Some reduction of the circulatory half-life was observed, from 10.5 days in control to 7.5 days after treatment with 10 J/$cm^2$ (FIG. 7). In preliminary studies in baboons, whose RBC are more similar to those of humans, treatment with liposomal Pc4 and 10 J/cm2 of 700 nm light had only slight effect on the circulatory half-life, reducing it from 13.2 days to 11.6 days (not shown). It should be noted that 24 hour recovery in vivo of the treated RBC always exceeded 90%.

Discussion

Enhancement of the specificity of Pc4 for virus inactivation in RBCC was studied using two different approaches. First, Pc4 was formulated in liposomes and the liposome compositions were optimized so that binding of Pc4 to red cells was minimized while maintaining good virus kill. Second, a light source LED array emitting a narrow band at 700 nm, corresponding to the spectrum region where Pc4-induced red cell damage is minimal and virus kill is significant, was selected (Ben-Hur, E., et al. *Lasers Med. Sci.* 11:221–225 (1996). When these two approaches were combined hemolysis following a virucidal light dose (10 J/$cm^2$) did not exceed 1% over 3 weeks storage and circulatory half-life and 24 hour recovery were close to normal in rabbits and essentially normal in baboons.

With regard to the liposome composition, a specific feature that makes liposomes optimal for delivery of Pc4 has not been identified. Attaching PEG and producing "stealth" liposomes, an approach used to prevent removal of liposomes by the reticuloendothelial system (Allen, T. M. *Trends Phar. Sci.* 15:215–220 (1994), enhanced Pc4 binding to red cells (Table 2), and resulted in massive hemolysis. Incorporation of cholesterol in the liposomes resulted in even higher Pc4 binding to red cells. Liposomes composed of the synthetic phospholipids POPC and DOPS gave optimal results. Interestingly, although increasing the ratio of the charged moiety DOPS from 9:1 to 1:1 resulted in progressively reduced binding of Pc4 to red cells (Table 2), minimal hemolysis was obtained with a ratio of 4:1 (FIG. 4). The reasons for this apparent discrepancy are not known. One possibility could be greater lability of the more negatively charged liposomes to photodynamic degradation during light exposure. The Pc4 released would be available for binding to red cells. Greater lability could result from the presence of two oleic acid moieties in DOPS compared to one in POPC. Unsaturated fatty acids are more prone to oxidative damage than saturated ones.

It is worthy of note that virucidal treatment (10 J/$cm^2$ of 700 nm light) which reduced the circulatory survival of rabbit red cells by about 30% (FIG. 7) had only a slight effect on baboon red cells. This is not surprising since rabbit red cells are more susceptible than primate red cells, as observed by us before using another phthalocyanine photosensitizer (Rywkin, S., et al. *Photochem. Photobiol.* 56:463–469 (1992); Horowitz, B., et al. *Blood Cells* 18:141–150 (1992)). Based on this result it is concluded that human red cells may also circulate normally after virucidal treatment with Pc4 and 700 nm light, and that this procedure is useful for sterilizing RBCC.

TABLE 1

Binding of Pc4 to RBC as a Function of Incubation Time and Delivery Vehicle[1]

| Incubation Time (min) | Pc4 Bound to RBC (%) DMSO | CRM | Liposomes[2] |
|---|---|---|---|
| 0 | 54 | 59 | 6 |
| 5 | 54 | 58 | 9 |
| 30 | 56 | 58 | 15 |
| 90 | 54 | 64 | 44 |

[1]Pc4 was added into RBCC at 2 μM final concentration. At various times thereafter at room temperature, RBC were separated by centrifugation, rinsed 5 times with PBS, and Pc4 was extracted and analyzed by HPLC, as described. Pc4 not bound to RBC was recovered quantitatively from the plasma.
[2]Liposomes were composed of POPC:DOPS = 9:1.

TABLE 2

Binding of Pc4 to RBC When Formulated in Various Liposomes[1]

| Liposomal Preparation | Pc4 Bound to RBC (%) |
|---|---|
| POPC:DOPS = 9:1 | 4.8 |
| POPC:DOPS = 4:1 | 4.4 |
| POPC:DOPS = 1:2 | 1.0 |
| POPC:DOPS = 1:1 | 0.8 |
| POPC:DOPS:PEG = 8:1:1 | 23.5 |
| POPC:DOPS:chol = 9:1:10 | 33.7 |

[1]Pc4 was added into RBCC at 2 μM final concentration formulated in the indicated liposomes. After 35 minutes at 4° C., RBC were separated by centrifugation, rinsed 5 times with PBS, and Pc4 was analyzed by HPLC, as described.

EXAMPLE 2

Pc4 was added at a final concentration of 2 μM, together with 4 mM cysteine, 1 mM tocopherol succinate and 0.5 mM carnitine, to 3 ml test tubes and 50 ml pediatric blood bags containing RBCC (50% hematocrit) spiked with VSV, BDV or HIV. Light exposure was at 670 nm from LED array at an irradiance of 20 mW/$cm^2$ (i.e. 10 minute exposure resulted in 12 J/$cm^2$). The dosages of light applied correspond to ≧6 $log_{10}$ virus kill, and were determined from inactivation kinetics (dose-response curve). The results of the virus kill are presented in Table 3 below, while the hemolysis of RBC during storage after virucidal treatment is presented in FIG. 8.

TABLE 3

Virus Inactivation in RBCC Using PC4 and Red Light

| Virus | Light Dose (J/cm2) | |
|---|---|---|
| | Test Tubes | Blood Bags |
| VSV | 5 | 22 |
| BDV | 7 | 30 |
| HIV (cell-free) | 15 | 55 |
| HIV (cell-assoc.) | 15[1] | 55 |

[1]At this dose there was only 4 $\log_{10}$ kill.

EXAMPLE 3

RBCC were treated with 2 μM Pc4 in POPC:DOPC=4:1 liposomes in the presence of 1 mM tocopherol succinate in the formulations presented in Table 4 below, and exposed to 10 J/cm² of red light (670 nm) emitted by LED array. The RBCC were then stored for 21 days at 4° C. The percentage of hemolysis for each formulation is presented in Table 4 below.

TABLE 4

| Formulation of α-tocopherol succinate (1 mM) | Hemolysis After 21 Day Storage (%) |
|---|---|
| Ethanol | 10.5 |
| POPC:DOPS = 4:1 | 18.3 |
| POPC:DOPS:chol = 9:1:10 | 6.1 |
| POPC | 1.2 |
| Untreated RBCC | 1.1 |

All publications and patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. A method for reducing the level of infectious virus that may be contained in a red blood cell composition comprising the steps of contacting composition with a photosensitizer formulated in a liposome carrier, and, after a period of time not greater than 30 minutes, exposing the composition to light at a sufficient wavelength, dose and duration to reduce the level of infectious virus contained in the composition;
said liposome carrier comprising 1-palmitoyl-2-oleoyl-sn-glycero-phosphocholine (POPC) and 1,2-dioleoyl-sn-glycero-3-(phospho-L-serine) (DOPS) at a ratio of 10:1–0.5:1.

2. The method of claim 1, wherein the red blood cell composition is whole blood or a red blood cell concentrate.

3. The method of claim 1, wherein the virus is selected from the group consisting of human immunodeficiency virus, Cytomegalovirus, Ebstein-Barr virus, Hepatitis B virus, Hepatitis C virus, and Herpes Simplex viruses.

4. The method of claim 1, wherein the photosensitizer is selected from the group consisting of a phthalocyanine, a porphyrin, a purpurin, a psoralen, a bergapten, an angelicin, a chlorin, and a flavin.

5. The method of claim 4 wherein the photosensitizer is a phthalocyanine.

6. The method of claim 5, wherein the phthalocyanine is an aluminum, germanium, gallium, tin or silicon phthalocyanine; a sulfonated- aluminum, germanium, gallium, tin or silicon phthalocyanine; or a nitrated-aluminum, germanium, gallium, tin or silicon phthalocyanine.

7. The method of claim 6, wherein the phthalocyanine is a sulfonated aluminum phthalocyanine.

8. The method of claim 7, wherein the sulfonated aluminum phthalocyanine is aluminum tetrasulfophthalocyanine or aluminum disulfophthalocyanine.

9. The method of claim 6, wherein the phthalocyanine is a silicon phthalocyanine.

10. The method of claim 9, wherein the silicon phthalocyanine is hydroxysiloxydimethylpropyl-N-dimethyl silicon phthalocyanine (Pc4).

11. The method of claim 10, wherein the concentration of Pc4 in the red blood cell composition is 0.5–10 μM.

12. The method of claim 10, wherein the concentration of Pc4 in the red blood cell composition is 1–5 μM.

13. The method of claim 1, wherein the light is applied ≦10 minutes after contacting the red blood cell composition with the photosensitizer formulated in the liposome carrier.

14. The method of claim 1, wherein the light is applied ≦5 minutes after contacting the red blood cell composition with the photosensitizer formulated in the liposome carrier.

15. The method of claim 1, wherein the light is applied at a wavelength that corresponds to the maximum absorption of the photosensitizer.

16. The method of claim 1, wherein the light is applied at a dose of 5–200 J/cm².

17. The method of claim 1, wherein the light is applied for 5 minutes to 3 hours.

18. The method of claim 1, wherein the ratio of POPC to DOPS is about 4:1.

19. The method of claim 1, which further comprises contacting the composition with at least one quencher before exposing the composition to light.

20. The method of claim 19, wherein the quencher is selected from the group consisting of flavonoids, vitamin C, vitamin E, glutathione, trolox, cysteine, ergothioneine, and other non-toxic quenchers.

21. The method of claim 19, wherein the quencher is formulated in a liposome carrier.

22. The method of claim 21, wherein the liposome carrier comprises at least one natural phospholipid, at least one synthetic phospholipid, or combinations thereof.

23. The method of claim 21, wherein the liposome carrier comprises cholesterol.

24. The method of claim 21, wherein the liposome carrier comprises soy phosphatidyl choline (PC).

25. The method of claim 21, wherein the liposome composition comprises 1-palmitoyl-2-oleoyl-sn-glycero-phosphocholine (POPC).

26. The method of claim 25, wherein the quencher is vitamin E.

27. The method of claim 26, wherein the ratio of vitamin E to POPC is 1:5–1:3.

28. The method of claim 26, wherein the ratio of vitamin E to POPC is about 1:3.7.

* * * * *